United States Patent [19]

Kasafírek et al.

[11] Patent Number: 4,528,133
[45] Date of Patent: Jul. 9, 1985

[54] BIOLOGICALLY ACTIVE TRIPEPTIDE AND TETRAPEPTIDE ALKYLAMIDES, AND METHOD FOR THE PREPARATION THEREOF

[75] Inventors: Evžen Kasafírek; Přemysl Frič; Jan Slabý; Alena Robalová, all of Prague, Czechoslovakia

[73] Assignee: SPOFA, spojene podniky pro zdravotnickou vyrobu, Prague, Czechoslovakia

[21] Appl. No.: 538,095

[22] Filed: Oct. 3, 1983

[30] Foreign Application Priority Data

Oct. 1, 1982 [CS] Czechoslovakia ............... 7013-82

[51] Int. Cl.³ ............................................. C07C 103/52
[52] U.S. Cl. ............................................. 260/112.5 R
[58] Field of Search .................. 260/112.5 R; 424/177

[56] References Cited

U.S. PATENT DOCUMENTS

| 4,155,916 | 5/1979 | Smith et al. | 260/345.2 |
| 4,167,449 | 9/1979 | Gargiulo et al. | 260/112.5 R |
| 4,187,216 | 2/1980 | Hassall et al. | 424/177 |
| 4,275,153 | 6/1981 | Gargiulo et al. | 260/112.5 R |
| 4,276,298 | 6/1981 | Jones et al. | 424/270 |
| 4,336,186 | 6/1982 | Gargiulo et al. | 260/112.5 R |
| 4,371,466 | 2/1983 | McGregor | 260/112.5 R |

FOREIGN PATENT DOCUMENTS 2624377  6/1980  Australia .

OTHER PUBLICATIONS

Biochem. and Biophys. Res. Commun., 32(1968), pp. 898–902.

Primary Examiner—Delbert P. Phillips

[57] ABSTRACT

This invention relates to biologically active tripeptide and tetrapeptide alkylamides of the general formula

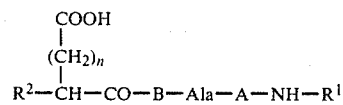

wherein
R$^1$ is an alkyl with 1 to 5 carbon atoms,
A is a peptidically bound alanine or proline residue,
B is a peptidically bound glycine, alanine or proline residue,
n is an integer of 1 or 2, and
R$^2$ is an alkylcarbonylamino group with 2 to 12 carbon atoms, an alkenyl with 6 to 12 carbon atoms or a benzyloxycarbonylamino group.

The compounds effectively inhibit the enzymatic activity of pancreatic and leucocytal elastase and are expected to find use in the treatment of acute pancreatitis, chronic obstructive pulmonary disease, pulmonary emphysema, and certain forms of arthritis. The invention also relates to processes for the preparation of the title compounds and to pharmaceutical compositions containing them.

12 Claims, No Drawings

BIOLOGICALLY ACTIVE TRIPEPTIDE AND TETRAPEPTIDE ALKYLAMIDES, AND METHOD FOR THE PREPARATION THEREOF

FIELD OF INVENTION

This invention relates to biologically active tripeptide and tetrapeptide alkylamides; to the preparation thereof; and to pharmaceutical compositions containing them. The alkylamides of the present invention are useful as inhibitors of the enzyme elastase.

BACKGROUND OF INVENTION

Elastase is an enzyme known to facilitate the digestion of elastin, collagen, and other elastic tissue by covalent catalysis. The enzyme combines with its substrate to form a highly reactive transitional compound. At the active sight of the enzyme, the hydroxyl group of a specific serine residue joins with an acyl group in the substrate to form an acyl-enzyme intermediate, thus rendering the substrate protein more vulnerable to decomposition. Inhibitors are known to suppress enzymatic catalysis by combining with the free enzyme, with the enzyme-substrate complex, or with both. Elastase is of pharmacological interest because of its presumed role in the pathology of certain diseases, such as pancreatitis, pulmonary emphysema, arthritis, and atheriosclerosis. Inhibitors of elastase are likewise of interest for their potential therapeutic value in the treatment of these diseases.

Alkylamides of dipeptides are known to be effective inhibitors of elastase (See Belgian Pat. Nos. 855,851 and 856,064). These dipeptides mimic the characteristics of amino acid compositions known to be preferred by elastase. Optimum substrate studies for pancreatic elastase have revealed the presence of a specific electrostatic bond between the enzyme and its substrate at a position toward the substrate's N-terminal. This bond is believed to be related to a primary interaction between substrate and enzyme. Synthetic elastolytic substances designed to induce this or a similar interaction are potential elastase inhibitors. See I. Schechter et al., Biochem. Biophys. Res. Commun. 32, 898 (1968); Eur. J. Biochem. 69, 1 (1976); FEBS Lett. 40, 353 (1974).

The earlier work revealed that the elastolytic hydrolysis of these synthetic substances could be enhanced by the presence of a carboxyl group in the N-terminal part of the inhibitor. The carboxyl group, as opposed to a hydrophobic residue (such as an acetyl) increased elastase inhibition in the same manner.

It is also known that the properties of an elastase inhibitor vary with the length of the peptide chain: tripeptides are more effective inhibitors than dipeptides. See U.S. patent application, Ser. No. 406,168 (Czechoslovakian Pat. No. PV 5977-81); Eur. J. Biochem. 69,1 (1976).

U.S. patent application Ser. No. 406,168 discloses certain carboxyalkanoylpeptide alkylamides that show significant elastase inhibiting properties and are physiologically tolerated. These synthetic peptides were observed to interact with the enzyme electrostatically, within their respective N-terminal regions. See Eur. J. Biochem. 69, 1 ( 1976); FEBS Lett. 40, 353 (1974). As previously known in the art, electrostatic coupling is induced by residues of dicarboxylic acids, e.g. succinic or glutaric acid.

In the present invention, the incorporation of aspartic or glutamic acid residues into the N-terminal region of the synthetic polypeptide inhibitor molecule, combined with appropriate N-acyl substitution, has been shown to induce similar electrostatic interactions. Thus, a new species of elastase inhibitors, and their method of preparation, is revealed.

SUMMARY OF INVENTION

Biologically active tripeptide and tetrapeptide alkylamides of the following general formula are disclosed:

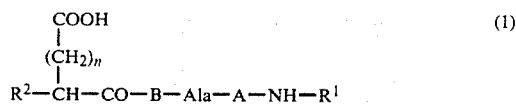

wherein
R¹ is an alkyl with 1 to 5 carbon atoms,
A is a peptidically bound alanine or proline residue,
B is a peptidically bound glycine, alanine or proline residue,
n is an integer of 1 or 2, and
R² is an alkylcarbonylamino group with 2 to 12 carbon atoms, an alkenyl with 6 to 12 carbon atoms or a benzyloxycarbonylamino group.

These compounds are formed by the incorporation of an aspartic or glutamic acid residue into the N-terminal portion of the peptide chain of the inhibitor molecule, followed by N-acyl substitution. This has been shown to create electrostatic interactions similar to those found in the earlier anionic inhibitors formed by incorporation of succinic and glutaric acid residues. Introduction of aspartic or glutamic acid residues, with their alpha-amino group, tends to weaken the anionic interaction of the carboxyl group. In the present invention, this partial intramolecular neutralization is suppressed by N-acyl substitution. It was observed with surprise that a hydrophobic residue adjacent to the carboxyl in the N-terminal part of the inhibitor molecule very markedly increased the elastase inhibiting activity of these anionic inhibitors. Moreover, N-acyl substitution is not limited to acylated aspartic and glutamic acid derivatives. A similar effect, with similar inhibition constants ($K_i$), was observed in the alkenyl derivatives of succinic and glutaric acid.

These novel anionic elastase inhibitors, with N-acylated residues of aspartic or glutamic acid, or with alkenyl substituted residues of succinic or glutaric acid, positioned within the N-terminal region of the synthetic inhibitor, model in some respects the structural units of the natural elastase substrate, elastin. (Elastin is known to contain an elevated ratio of acidic and hydrophobic amino acids.) The elastolytic substrates of the present invention showed in vitro high inhibitory activity towards pancreatic and leucocytal elastase. The laboratory test results are summarized in Table I.

The elastase inhibitors of the present invention are completely free of unnatural moieties and groups. It is anticipated that this will permit therapeutic use with little or no side effects.

TABLE I

Inhibition Constants (K$_i$) of the Elastase Inhibitors

| Inhibitor | PE<br>Glt—(Ala)$_4$—Nan<br>Suc—(Ala)$_4$—Nan | LE<br>Glt—(Ala)$_3$—Val—Nan |
|---|---|---|
| Ac—Asp—Ala—Pro—NH—iBu | 0.12<br>0.19 | 0.191 |
| Ac—Asp—Pro—Ala—Ala—NH—Et | 0.034<br>0.025 | 1.0 |
| Btr—Glu—Ala—Ala—Pro—NH—Pr | 0.193<br>0.178 | 0.18 |
| Btr—Asp—Ala—Ala—Pro—NH—iBu | 0.12<br>0.12 | 0.136 |
| Dde—Ala—Ala—Ala—NH—Et | 0.0018<br>0.0025 | no inhibition |
| Dde—Ala—Ala—Ala—NH—iBu | 0.093<br>0.099 | 0.515 |
| Dde—Ala—Ala—Pro—NH—Pr | 0.0006<br>0.0005 | 0.10 |
| UDA—Asp—Ala—Ala—Pro—NH—Et | 0.0054<br>— | 0.012 |
| Z—Glu—Ala—Ala—Ala—NH—Et | 0.173<br>0.028 | 0.72 |

Ac — acetyl
Et — ethyl
iBu — isobutyl
UDA — undecanoyl
Z — benzyloxycarbonyl
PE — pancreatic elastase
Btr — butyryl
Pr — propyl
Suc — succinyl(i.e. 3-carboxypropionyl)
Glt — glutaryl(i.e., 4-carboxybutyryl)
Dde — 2-dodecenyl-succinyl
LE — leucocytal elastase.

An advantageous method for the preparation of alkylamides of the general formula 1 comprises the reaction of a compound of the general formula 2:

$$H—B—Ala—A—NH—R^1 \quad (2)$$

wherein
R$^1$, A and B are defined as in formula 1 and H is a hydrogen atom;
with a compound of the general formula 3:

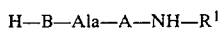

$$\begin{array}{c}COOR^3\\|\\(CH_2)_n\\|\\R^2—CH—COOH\end{array} \quad (3)$$

wherein
R$^2$ and n are defined as in formula 1 and R$^3$ is an alkyl with 1 to 4 carbon atoms or an aralkyl with 7 carbon atoms;
and subsequent elimination of the protective group R$^3$ from the intermediary compound of the general formula 4:

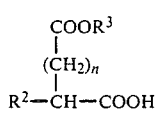

$$\begin{array}{c}COOR^3\\|\\(CH_2)_n\\|\\R^2—CH—CO—B—Ala—A—NH—R^1\end{array} \quad (4)$$

wherein
R$^1$, R$^2$, R$^3$, A, B and n are as defined above.

In another process for the preparation of compounds of the general formula 1, a compound of the general formula 2 is reacted with a compound of the general formula 5:

$$\begin{array}{c}COOR^3\\|\\(CH_2)_n\\|\\Y—NH—CH—COOH\end{array} \quad (5)$$

wherein
R$^3$ and n are defined as in formula 3 and
Y is a protective group,
to give a compound of the general formula 6:

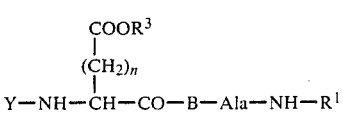

$$\begin{array}{c}COOR^3\\|\\(CH_2)_n\\|\\Y—NH—CH—CO—B—Ala—NH—R^1\end{array} \quad (6)$$

wherein
R$^1$, A, B and n are defined as in formula 1,
R$^3$ is defined as in formula 3, and
Y is defined as in formula 5;
whereafter the protective groups R$^3$ and/or Y are eliminated and the intermediary product is combined with a reactive derivative of a carboxylic acid of the general formula 7:

$$R^2—COOH \quad (7)$$

wherein
R$^2$ is defined as in formula 1, except that the alkenyl group preferably contains its anhydride, halide or ester.

If necessary, the remaining protective group is eliminated.

Still another process for the preparation of compounds of the general formula 1 consists in the reaction of a compound of the general formula 2 with a reactive derivative of a dicarboxylic acid of the general formula 8:

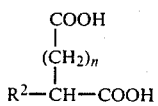

wherein
$R^2$ and n are defined as in formula 1, and
$R^2$ preferably contains its anhydride, monohalide or ester.

The preparation of the biologically active peptide derivatives of the present invention can be conducted by fragment condensation in a solution; or by successive (step-wise) construction from the corresponding amino acid derivatives in a solution or on a solid carrier.

Suitable protective groups for the intermediates are, for example, the urethane-type groups (e.g., a benzyloxycarbonyl); groups removable by mild acid hydrolysis (e.g., a tert-butyloxycarbonyl or o-nitrobenzenesulphenyl group); or groups removable electrolytically or by reduction with a metal (e.g., a 2-haloethyloxycarbonyl group).

The condensation reactions can be performed by azide, carbodiimide or mixed-anhydride methods, or by other techniques adapted to the preparation of peptides.

PREFERRED EMBODIMENTS

Further particulars of the procedure are illustrated by the following examples. The identity and purity of the products was verified by elemental analysis; the found values correspond to those calculated within narrow tolerance limits.

These examples are merely for purposes of exposition and are not to be construed as limiting.

Abbreviations

Asp(OBzl)—aspartyl beta-benzyl ester
Glu(OBzl)—glutamyl gamma-benzyl ester
Pro-NH$_2$—proline amide
BOC—tert-butyloxycarbonyl
Cpr—caproyl
Ac—Acetyl
Btr—butyryl
Et—ethyl
Pr—propyl
iBu—isobutyl
suc—succinyl
glt—glutaryl
Dde—2-dodecenyl-succinyl

EXAMPLE 1

N$^\alpha$-Acetylaspartyl-alanyl-alanyl-proline isobutylamide

A solution containing 2 mmoles (530 mg) of Ac-Asp(OBzl)[acetylaspartyl beta-benzyl ester] and 2 mmoles (630 mg) of Ala-Ala-Pro-NH-IBu[alanyl-alanyl-proline isobutylamide] in 20 ml of dimethylformamide is cooled to $-20°$ C. and treated with 440 mg of N,N'-dicyclohexyl carbodiimide. After 3 hours of stirring at 0° C. and 12 hours of standing at room temperature, the N,N'-dicyclohexyl urea precipitate is filtered off and washed with dimethylformamide. The filtrate is evaporated, and the residue is mixed with 8 ml of AcOEt at 30° C. The undissolved material is filtered off and washed with 2 ml of the same solvent. After 12 hours of standing at 3° C., the combined AcOEt solution crystallizes to yield 540 mg (45%) of Ac-Asp(OBzl)-Ala-Ala-Pro-NH-iBu[acetylaspartyl beta-benzyl-alanyl-alanyl-proline isobutylamide]. The analytical sample is crystallized similarly; m.p. 176°–179° C.

A solution containing 0.7 mmoles (440 mg) of the preceding compound in 20 ml MeOH, with 0.5 ml AcOH and 50 mg Pd black, is saturated with hydrogen for 2 hours. The catalyst is filtered off, washed with MeOH, and the filtrate is evaporated. The noncrystalline residue is dissolved in 15 ml AcOEt and, after 12 hours of standing at 3° C., the crystalline product is separated, washed with AcOEt and petroleum ether and dried to constant weight. The yield is 245 mg of the title product, N$^\alpha$-Acetylasparatyl-alanyl-alanyl-proline isobutylamide, m.p. 127°–130° C. (from 2-propanol—AcOEt).

EXAMPLE 2

N$^\alpha$-Butyrylaspartyl-alanyl-alanyl-proline isobutylamide

A solution containing 5 mmoles (1.6 g) BOC-Asp(OBzl)[tert-butyloxycarbonylaspartyl beta-benzyl ester] and 5 mmoles (1.56 g)Ala-Ala-Pro-NH-IBu[alanyl-alanyl-proline isobutylamide] in 66 ml dimethylformamide is cooled to $-20°$ C. and treated with 1.1 g N,N'-dicyclohexyl carbodiimide. After 3 hours of stirring at 0° C. and 12 hours of standing at room temperature, the N,N'-dicyclohexyl urea precipitate is filtered off, washed with dimethylformamide and the filtrate is evaporated. The residue is dissolved in 60 ml CH$_2$Cl$_2$ and the solution is successively shaken with 1% citric acid, 5% NaHCO$_3$ and water, dried over Na$_2$SO$_4$, and evaporated. Drying is completed by azeotropic distillation with benzene—tetrahydrofuran. The noncrystalline residue, BOC-Asp(OBzl)-Ala-Ala-Pro-NH-iBu[tert-butyloxycarbonylasparatyl alanyl-alanyl-proline isobutylamide], is dissolved in 5 ml glacial AcOH to which a 5 ml solution of 2.9M HCl—AcOH is added. After standing for 3 hours, the formed hydrochloride is precipitated with 150 ml of ether, decanted with the same solvent, and dried in a desiccator over NaOH and P$_2$O$_5$ to give noncrystalline, chromatographically homogeneous foamy Asp(OBzl)-Ala-Ala-Pro-NH-iBu.HCl[aspartyl beta-benzyl-alanyl-alanyl-proline isobutylhydrochloride]; R$_f$=0.30/S$_1$, 0.80/S$_2$.

S$_1$: n-butanol—AcOH—water 4:1:1;
S$_2$: n-butanol—AcOH—pyridine—water 15:3:10:6.

The preceding product is dissolved in 20 ml water and 5 ml of a saturated aqueous NaHCO$_3$ solution is added. On cooling to 5° C., a solution of 1 ml butyric anhydride in 5 ml tetrahydrofuran is introduced by the drop over a 30 minute period. After stirring and cooling for another 30 minutes, the solution is evaporated, the residue is suspended in 10 ml of hot AcOEt, the salt precipitate is filtered off, washed with 5 ml of the same solvent, and the filtrate is allowed to crystallize for 12 hours at 3° C. The crystals are separated, washed successively with AcOEt and petroleum ether, and dried to constant weight. The yield is 350 mg of Btr-Asp(OBzl)-Ala-Ala-Pro-NH-iBu[butyrylaspartyl beta-benzyl-alanyl-alanyl-proline isobutylamide], m.p. 149°–151° C. (AcOEt). Hydrogenolysis by the procedure described for Ac-Asp in Example 1 yields the title product, N-Butyrylaspartyl-alanyl-alanyl-proline isobutylamide (76%), m.p. 180°–183° C. (2-propanol—AcOEt).

EXAMPLE 3

N$^\alpha$-caproylglutamyl-alanyl-alanyl-alanine isobutylamide

A solution containing 2 mmoles (665 mg) BOC-Glu(OBzl)[tert-butyloxycarbonyl glutamyl gamma-benzyl ester] and 2 mmoles (573 mg) Ala-Ala-Ala-NH-iBu[alanyl-alanyl-alanine isobutylamide] in 15 ml dimethylformamide is cooled to −20° C. and treated with 440 mg of N,N'-dicyclohexyl carbodiimide. The mixture is stirred at 0° C. for 3 hours and allowed to stand at room temperature for 12 hours. The N,N'-dicyclohexyl urea precipitate is filtered off, washed with dimethylformamide and the filtrate is evaporated. The solid residue is dissolved in AcOEt, successively washed with 1% citric acid, 5% NaHCO$_3$ and water, the solution is evaporated, and the residue is crystallized from 15 ml of boiling 2-propanol by addition of 150 ml of petroleum ether. The product obtained is 670 mg (55%) of BOC-Glu(OBzl)-Ala-Ala-Ala-NH-iBu[tert-butyloxycarbonyl glutamyl gamma-benzyl alanyl-alanyl-alanine isobutylamide]; m.p. 199°–203° C. Acidolysis by the procedure in Example 2 gives Glu(OBzl)-Ala-Ala-Ala-NH-iBu.HCl[glutamyl gamma-benzyl alanyl-alanyl-alanine isobutylhydrochloride] in a yield of 69%. R$_f$=0.20/S$_1$, 0.75/S$_2$.

A solution containing 0.7 mmoles (360 mg) of this product in 10 ml tetrahydrofuran and 40 ml of 2.5% aqueous NaHCO$_3$, cooled to 10° C., is treated with a solution of 145 mg caproylchloride in 2 ml tetrahydrofuran added in two portions during 15 minutes. After stirring for 1 hour, the reaction mixture is adjusted to pH 4 with 1M HCl, the solvent is evaporated and the aqueous solution is acidified to pH 2. After 12 hours of standing at 3° C., the crystalline product is collected, washed with water, and dried to constant weight to give 290 mg of Cpr-Glu(OBzl)-Ala-Ala-Ala-NH-iBu[caproylglutamyl gamma-benzyl alanyl-alanyl-alanine isobutylamide]; m.p. 266°–270° C. (2-propanol—AcOEt). Hydrogenolysis by the procedure in Example 1 gives the title product N$^\alpha$-caproylglutamyl-alanyl-alanyl-alanine isobutylamide in a yield of 63%; m.p. 224°–227° C.

EXAMPLE 4

N-(2-Dodecenylsuccinyl)alanyl-alanyl-alanine ethylamide

A solution containing 2 mmoles (520 mg) of Ala-Ala-Al;a-NH-Et[alanyl-alanyl-alanine ethyl amide] 10 ml of dimethylformamide is treated with 1.05 g of 2-dodecenylsuccinic anhydride. The mixture is warmed for 1 hour at 70° C., the solvent is evaporated and petroleum ether is added to precipitate the product. Crystallisation from 2-propanol and petroleum ether produces a 72% yield of Dde-Ala-Ala-Ala-NH-Et[2-dodecenylsuccinyl alanyl-alanyl alanine ethylamide]; m.p. 225°–229° C. The analytical sample is crystallized similarly and melts at 231°–234° C. R$_f$=0.73/S$_1$, 0.78/S$_2$.($\alpha$)$_D^{20}$=−4.08°; c=0.2 (dimethylformamide).

EXAMPLE 5

N-(2-Dodecenylsuccinyl)alanyl-alanyl-proline propylamide

This compound is obtained through a procedure similar to that employed in Example 4. The yield is 66%, m.p. 97°–99° C.

($\alpha$)$_D^{20}$=−48.8°; c=0.2 (dimethylformamide).

EXAMPLE 6

N$^\alpha$-Benzyloxycarbonylglutamyl-alanyl-alanyl-proline ethylamide

A solution containing 2 mmoles (600 mg) of Ala-Ala-Pro-NH-Et[alanyl-alanyl-proline ethylamide] in 10 ml dimethylformamide is treated with 2.4 mmoles (600 mg) of Z-glutamic acid anhydride. After 1 hour of warming at 60° C., the reaction mixture is evaporated, the non-crystalline residue is mixed with 30 ml AcOEt and, after 12 hours of standing at 3° C., the crystals are collected on a filter and washed successively with AcOEt and petroleum ether. The yield is 1.1 g of crude product, m.p. 75°–80° C. On crystallization from AcOET and petroleum ether, the pure substance melts at 101°–103° C.

EXAMPLE 7

N$^\alpha$-Acetylaspartyl-glycyl-alanyl-alanyl-proline isobutylamide

A solution containing 28 mmoles (7.84 g) of Z-Gly-Ala and 3.92 g of N-hydroxybenzotriazole in 50 ml CHCl$_3$ and 30 ml dimethylformamide is mixed with a second solution containing 28 mmoles Pro-NH-iBu[proline isobutylamide] in 56 ml of CHCl$_3$. The mixture is cooled to −5° C. and treated with 6.61 g of N,N'-dicyclohexyl carbodiimide. After 2 hours of stirring at 0° C. and 3 hours at room temperature, the N,N'-dicyclohexyl urea precipitate is filtered off, the filtrate is evaporated, the residue is dissolved in butanol and successively shaken with 1% citric acid, 5% NaHCO$_3$ and water, dried over Na$_2$SO$_4$ and evaporated. Crystallisation from AcOEt gives 4.5 g Z-Gly-Ala-pro-NH-iBu in a yield of 37%. On repeated crystallization by the same procedure, the pure substance melts at 135°–137° C., ($\alpha$)$_D^{20}$=−72.7°; c=0.2 (dimethylformamide). Condensation with Ac-Asp(OBzl)[acetylasparatyl beta-benzyl ester] by the procedure in Example 1 gives Ac-Asp(OBzl)-Gly-Ala-Pro-NH-iBu[acetylasparatyl beta-benzyl glycyl-alanyl-proline isobutylamide] in a yield of 52%; m.p. 185°–190° C. Hdrogenolysis by the procedure in Example 1 produces the title product, N$^\alpha$-Acetylaspartyl-glycyl-alanyl-alanyl-proline isobutylamide; m.p. 142°–146° C.

EXAMPLE 8

N$^\alpha$-Undecanoylaspartyl-alanyl-alanyl-proline ethylamide

Condensation of BOC-Asp(OBzl) with Ala-Ala-Pro-NH-Et is achieved by the carbodiimide method as described in Example 1. Subsequent debenzylation by the procedure in Example 1 gives BOC-Asp-Ala-Ala-Pro-NH-Et in a yield of 68%; R$_f$=0.75(S)$_1$. Acylation with undecanolylchloride, by the procedure in Example 3, produces the title product, N$^\alpha$-Undecanoylaspartyl-alanyl-alanyl-proline ethylamide; m.p. 184°–189° C. (from water). Amino acid composition analysis yields; Asp 1.02, Pro 1.04, Ala 1.97.

EXAMPLE 9

N$^\alpha$-Acetylaspartyl-prolyl-alanyl-alanine ethylamide

The condensation of Z-Pro-Ala with Ala-NH-Et by the procedure in Example 7 yields Z-Pro-Ala-Ala-NH-Et; m.p. 219°–220° C. from 2-propanol—AcOEt); ($\alpha$)$_D^{20}$=−36.2°; c=0.2 (dimethylformamide). This intermediate is successively converted, as described in Example 2, into (1) BOC-Asp(Obzl)-Pro-Ala-Ala-NH-Et, m.p. 133°–136° C. (AcOEt—petroleum ether), $(\alpha)_D^{20} = -61.1°$, c=0.2 (MeOH); (2) Asp(OBzl)-Pro-Ala-Ala-NH-Et.HCl, m.p. 189°–193° C. (MeOH—Et$_2$O), and (3) Ac-Asp(OBzl(-Pro-Ala-Ala-NH-Et, m.p. 191°–193° C. (AcOEt—petroleum ether), $(\alpha)_D^{20} = -68.5°$, c=0.2 (MeOH). Hydrogenolysis of the latter product by the procedure in Example 1 yields the title compound, N$^\alpha$-Acetylaspartyl-prolyl-alanyl-alanine ethylamide; m.p. 153°–155° C. (melting begins at 143° C.).

We claim:

1. Biologically active tripeptide and tetrapeptide alkylamide of the formula

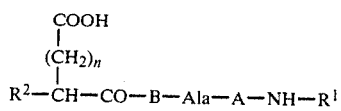

wherein
(a) R$^1$ is selected from the group consisting of alkyl groups of 1 to 5 carbon atoms,
(b) A is a peptidically bound residue selected from the group consisting of alanine and proline,
(c) B is a peptidically bound residue selected from the group consisting of glycine, alanine and proline,
(d) n is an integer of 1 or 2, and
(e) R$^2$ is selected from the group consisting of alkylcarbonylamino groups of 2 to 12 carbon atoms, alkenyl groups of 6 to 12 carbon atoms, and benzyloxycarbonylamino groups.

2. N$^\alpha$-Acetylaspartyl-alanyl-alanyl-proline isobutylamide.

3. N$^\alpha$-Butyrylaspartyl-alanyl-alanyl-proline isobutylamide.

4. N-Capryglutamyl-alanyl-alanyl-alanine isobutylamide.

5. 2-Dodecenylsuccinyl-alanyl-alanyl-alanine ethylamide.

6. 2-Dodecenylsuccinyl-alanyl-alanyl-proline propylamide.

7. Benzyloxycarbonylglutamyl-alanyl-alanyl-proline ethylamide.

8. Benzyloxycarbonylglycyl-alanyl-proline isobutylamide.

9. N$^\alpha$-Acetylaspartyl-glycyl-alanyl-proline isobutylamide.

10. N$^\alpha$-Undecanoylaspartyl-alanyl-alanyl-proline ethylamide.

11. Benzyloxycarbonylprolyl-alanyl-alanine ethylamide.

12. N$^\alpha$-Acetylaspartyl-propyl-alanyl-alanine ethylamide.

* * * * *